(12) United States Patent
Kim et al.

(10) Patent No.: US 11,400,085 B2
(45) Date of Patent: Aug. 2, 2022

(54) METHOD FOR PREPARING PHARMACEUTICAL COMPOSITION FOR PREVENTING OR TREATING COGNITIVE IMPAIRMENT-RELATED DISEASE AND PHARMACEUTICAL COMPOSITION FOR PREVENTING OR TREATING COGNITIVE IMPAIRMENT-RELATED DISEASE PREPARED BY THE SAME

(71) Applicant: INVENTAGE LAB INC., Seongnam-si (KR)

(72) Inventors: Ju Hee Kim, Seongnam-si (KR); Sang No Lee, Seoul (KR)

(73) Assignee: INVENTAGE LAB INC., Seongnam-si (KR)

( * ) Notice: Subject to any disclaimer, the term of this patent is extended or adjusted under 35 U.S.C. 154(b) by 0 days.

(21) Appl. No.: 16/652,065

(22) PCT Filed: Mar. 19, 2019

(86) PCT No.: PCT/KR2019/003158
§ 371 (c)(1),
(2) Date: Mar. 29, 2020

(87) PCT Pub. No.: WO2019/182319
PCT Pub. Date: Sep. 26, 2019

(65) Prior Publication Data
US 2020/0246319 A1    Aug. 6, 2020

(30) Foreign Application Priority Data

Mar. 20, 2018 (KR) .................. 10-2018-0031972
Mar. 18, 2019 (KR) .................. 10-2019-0030801

(51) Int. Cl.
*A61K 31/445* (2006.01)
*A61K 9/16* (2006.01)

(52) U.S. Cl.
CPC .......... *A61K 31/445* (2013.01); *A61K 9/1647* (2013.01); *A61K 9/1682* (2013.01)

(58) Field of Classification Search
CPC .......................... A61K 31/445; A61K 9/1647
See application file for complete search history.

(56) References Cited

U.S. PATENT DOCUMENTS

| 2009/0014360 A1* | 1/2009 | Toner ............... B01D 45/12 209/208 |
| 2016/0022583 A1* | 1/2016 | Lee .................. A61K 9/0073 424/489 |

FOREIGN PATENT DOCUMENTS

| CN | 106422045 A | 2/2017 |
| KR | 100599350 B1 | 7/2006 |
| KR | 20080056731 A | 6/2008 |
| KR | 20140120496 A | 10/2014 |
| KR | 101472916 B1 | 12/2014 |
| KR | 1020160111039 A | 9/2016 |
| KR | 1020170009700 A | 1/2017 |

OTHER PUBLICATIONS

Petersen, The New England Journal of Medicine, 352, 23, 2005 (Year: 2005).*
International Search Report of PCT/KR2019/003158, dated Jun. 10, 2019, English translation.

* cited by examiner

Primary Examiner — Robert A Wax
Assistant Examiner — William Craigo
(74) Attorney, Agent, or Firm — STIP Law Group, LLC

(57) ABSTRACT

The present invention relates to a method for preparing a pharmaceutical composition for preventing or treating a cognitive impairment-related disease and a pharmaceutical composition for preventing or treating a cognitive impairment-related disease prepared by the same, and the pharmaceutical composition includes microparticles including donepezil and a biodegradable polymer, and the microparticles are in a form in which donepezil is uniformly distributed in a spherical biodegradable polymer. The present invention may maintain the effect of preventing or treating the cognitive impairment-related disease for 1 month by a single injection in order to eliminate the inconvenience of having to take the composition daily, and as the present invention is prepared by maintaining the average diameters of the particles at a predetermined micrometer size, a foreign body sensation and pain during administration into a patient as an injection is reduced, thereby enabling administration as an injection to be facilitated.

8 Claims, 3 Drawing Sheets

METHOD FOR PREPARING PHARMACEUTICAL COMPOSITION FOR PREVENTING OR TREATING COGNITIVE IMPAIRMENT-RELATED DISEASE AND PHARMACEUTICAL COMPOSITION FOR PREVENTING OR TREATING COGNITIVE IMPAIRMENT-RELATED DISEASE PREPARED BY THE SAME

CROSS-REFERENCE TO RELATED APPLICATIONS

This application is the U.S. National Phase under 35 U.S.C. § 371 of International Application No. PCT/KR2019/003158 filed on Mar. 19, 2019, which in turn claims the benefit of Korean Applications No. 10-2018-0031972 filed on Mar. 20, 2018, and 10-2019-0030801 filed on Mar. 18, 2019, the disclosures of which are incorporated by reference into the present application.

TECHNICAL FIELD

The present invention relates to a method for preparing a pharmaceutical composition for preventing or treating a cognitive impairment-related disease and a pharmaceutical composition for preventing or treating a cognitive impairment-related disease prepared by the same, and more particularly, to a method for preparing a pharmaceutical composition for preventing or treating a cognitive impairment-related disease, which may prepare microparticles in which donepezil is uniformly distributed into a uniform particle size, and a composition prepared by the same.

BACKGROUND ART

Dementia comprehensively encompasses complex clinical syndromes from which the brain is temperamentally impaired or destroyed by a variety of causes, such as acquired traumas or diseases, or genetic factors, and thus, leads to abnormal deterioration of overall cognitive functions and higher mental functions such as language, learning, and intelligence. Dementia may be largely divided into dementia caused by Alzheimer's disease, vascular dementia, dementia caused by specific cerebral disease and systemic disease, and the like according to the cause of disease, and dementia caused by Alzheimer's disease is responsible for 50% or more of them. Alzheimer-type dementia progresses due to the accumulation of β-amyloid, which is the causative protein of the dementia into oligomer and fibrile stages in the brain, and then in the form of plaque, during which process damage to the brain including neuron cells is caused, and thus the disease progresses.

Therapeutic agents developed to date have been developed in the direction of increasing the level of acetylcholine in the brain or increasing the activity of cholinergic neuron cells by focusing on the fact that a substance called acetylcholine is reduced in the brain of patients with Alzheimer-type dementia compared to normal people. Since acetylcholinesterase is an enzyme that hydrolyzes acetylcholine into choline and acetate, an acetylcholinesterase inhibitor has been used as a therapeutic agent for Alzheimer's dementia.

Such therapeutic agents for dementia are, for example, donepezil (trade name: ARICEPT), rivastigmin (trade name: EXELON) and galantamine (trade name: REMINYL).

The existing oral dementia therapeutic agents as described above may alleviate the symptoms of dementia only when a predetermined amount of dose is taken regularly every day, but have a disadvantage in that in the case of a patient with dementia, it is not easy to regularly take the therapeutic agent due to the characteristics of the disease.

Thus, there is a need for developing a long-lasting complex therapeutic agent capable of exhibiting a therapeutic effect for dementia for a long period of one month or more with a single administration via injection dosage form.

PRIOR ART DOCUMENT

Patent Document (Patent Document 1) KR 10-2008-0056731 A1

DISCLOSURE

Technical Problem

An object of the present invention is to provide a method for preparing a pharmaceutical composition for preventing or treating a cognitive impairment-related disease and a pharmaceutical composition for preventing or treating a cognitive impairment-related disease prepared by the same.

Another object of the present invention is to provide a method for preparing a pharmaceutical composition for preventing or treating a cognitive impairment-related disease, which may maintain the effect of preventing or treating the cognitive impairment-related disease for 1 month by a single injection in order to eliminate the inconvenience of having to take the composition daily, and a pharmaceutical composition for preventing or treating a cognitive impairment-related disease prepared by the same.

Still another object of the present invention is to provide a method for preparing a pharmaceutical composition for preventing or treating a cognitive impairment-related disease, which may facilitate administration as an injection by enabling the composition to maintain a constant blood concentration for a target period and reducing a foreign body sensation and pain when the composition is administered to a patient as an injection as the composition is prepared by maintaining the average diameter of particles at a constant micrometer size, and a pharmaceutical composition for preventing or treating a cognitive impairment-related disease prepared by the same.

Technical Solution

To achieve the objects, a method for preparing a pharmaceutical composition for preventing or treating a cognitive impairment-related disease according to an exemplary embodiment of the present invention may include: 1) preparing a first mixture by dissolving a biodegradable polymer and donepezil in an organic solvent; 2) preparing a second mixture by dissolving a surfactant in water; 3) infusing the first mixture in Step 1) into a microchannel in a straight-line direction and allowing the first mixture to flow; 4) preparing microparticles in which donepezil is uniformly distributed in spherical biodegradable polymer particles by infusing the second mixture in Step 2) into a microchannel formed on both side surfaces or one side surface thereof and allowing the second mixture to flow such that the first mixture in Step 3) can form an intersection point with a microchannel flowing in a straight-line direction, and intersecting a flow of the first mixture in a straight-line direction with a flow of the second mixture; 5) collecting the microparticles produced at the intersection point in Step 4); 6) removing an organic solvent present on the surface of the microparticles by stirring the microparticles collected in Step 5); and 7) washing the microparticles in Step 6) and drying the microparticles.

The donepezil may be included in a form of donepezil or a pharmaceutically acceptable salt thereof.

The microparticles have an average diameter of 30 to 70 µm.

The microparticles may maintain the effect of preventing or treating a cognitive impairment-related disease by sustainably releasing donepezil for 1 month.

The biodegradable polymer may be selected from the group consisting of polylactic acid, polylactide, poly(lactic-co-glycolic acid), poly(lactide-co-glycolide)(PLGA), polyphosphazene, polyiminocarbonate, polyphosphoester, polyanhydride, polyorthoester, polycaprolactone, polyhydroxyvalerate, polyhydroxybutyrate, polyamino acid, and a combination thereof.

For the microparticles, a microchannel is used in order to prepare the microparticles, and a width (w) of a cross section of the channel is within a ratio range of 0.7 to 1.3 for an average diameter (d') of the microparticles.

For the microparticles, a microchannel is used in order to prepare the microparticles, and a height (d) of a cross section of the channel is within a ratio range of 0.7 to 1.3 for an average diameter (d') of the microparticles.

The cognitive impairment-related disease is dementia, Alzheimer's disease, amnesia, or Parkinson's disease.

A pharmaceutical composition for preventing or treating a cognitive impairment-related disease according to another exemplary embodiment of the present invention includes microparticle including donepezil and a biodegradable polymer, the microparticles are in a form in which donepezil is uniformly distributed in a spherical biodegradable polymer, and the microparticles may be prepared to have a uniform particle size by the preparation method.

Hereinafter, the present invention will be described in more detail.

Alzheimer's disease is representative of a cognitive impairment-related disease, and Alzheimer's disease is the most common degenerative brain disease that causes dementia and was first reported by Dr. Alois Alzheimer, a German psychiatrist in 1907. Alzheimer's disease develops slowly and progresses gradually, initially displays memory impairment for recent events, is gradually accompanied by disorders of other cognitive functions, such as language function and judgment, and eventually loses all daily functions.

Although the exact pathogenesis and the cause of Alzheimer's disease are currently unknown, an abnormal phenomenon such as the aggregation of amyloid-beta (Aβ) and tau proteins present in the brain is observed as a pathological feature. Accordingly, the amyloid-beta and tau proteins have been used as biomarkers for diagnosis of Alzheimer's disease.

Currently commercially available therapeutic agents for Alzheimer's disease are classified into 'AChE inhibitors', which prevent the degradation of the neurotransmitter acetylcholine, and 'NMDA receptor antagonists', which prevent glutamic acid from binding to receptors and being excessively activated.

Among them, donepezil has been used as an 'AChE inhibitor', which prevents the degradation of the neurotransmitter acetylcholine.

The donepezil is included in a form of donepezil or a pharmaceutically acceptable salt thereof, and donepezil is a drug used for treating Alzheimer-type mild, moderate and severe dementia symptoms, preventing Alzheimer-type mild cognitive impairment, and preventing or treating Down syndrome, multiple sclerosis, Parkinson's disease, multi-infarct dementia, traumatic brain injury, and the like by reversibly and non-competitively inhibiting to increase the concentration of acetylcholine in the synapse.

Donepezil is a compound represented by the following Formula 1:

[Formula 1]

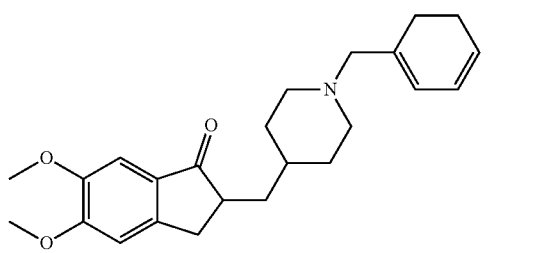

However, there is a problem in that these therapeutic agents need to be taken daily in order to prevent or treat a cognitive impairment-related disease.

Thus, the present invention may solve the problem in that a therapeutic agent needs to be taken daily in order to prevent or treat a cognitive impairment-related disease as a pharmaceutical composition for preventing or treating a cognitive impairment-related disease, including donepezil is provided as a dosage form which can be sustained for a long period of 1 month.

Further, compared to the case where the pharmaceutical composition is taken via oral administration, the present invention is excellent in the effects of preventing or treating a cognitive impairment-related disease by maintaining an effective blood concentration for a predetermined period due to the characteristics of a long-lasting injection, which is sustainably released at a constant level in vivo even when the initial dose is set at a low level.

That is, when the composition is taken via oral administration, there are problems in that lesions such as gastrointestinal disorders may occur in the digestive organs, and a predetermined amount or more of donepezil needs to be taken regularly every day for the effect of preventing or treating a cognitive impairment-related disease.

In contrast, the pharmaceutical composition for preventing or treating a cognitive impairment-related disease according to the present invention is administered to a subcutaneous fat or a wide area of muscle tissue where pain may be felt less in an injection dosage form, and as a biodegradable polymer surrounding donepezil as an active ingredient is degraded slowly in vivo, donepezil is sustainably released for 1 month, and the bioavailability is higher than that when the pharmaceutical composition is orally administered, so that despite the smaller dose than oral administration, the effect of preventing or treating a cognitive impairment-related disease due to high bioavailability is excellent.

The present invention includes microparticles including donepezil and a biodegradable polymer, and the microparticles are in a form in which donepezil is uniformly distributed in a spherical biodegradable polymer.

That is, by preparing biodegradable polymer microparticles containing donepezil, and then administering the biodegradable polymer microparticles, it is possible to exhibit an effect in which the donepezil is sustainably released as the biodegradable polymer of the microparticles is degraded in vivo.

The microparticles have an average diameter of 30 to 70 μm. When the microparticles have an average diameter of less than 30 μm, it is more likely that the microparticles will be eaten by macrophages after infusion into the human body, thereby affecting effective drug release and in vivo absorption. In addition, when the microparticles have an average diameter of more than 70 μm, there are problems in that a foreign body sensation and pain may be increased during the administration of the injection and the particle size distribution of the prepared particles is increased, and as a result, it is difficult to prepare microparticles having a uniform particle size. Furthermore, the administration of uniform microparticles having an average diameter of 30 to 70 μm may aid in the control of drug release in vivo constantly to maintain an effective blood concentration.

Thus, it is indispensable to prepare microparticles having a uniform particle size as the microparticles are prepared by the preparation method of the present invention described below.

As a method for preparing microparticles using a biodegradable polymer in the related art, a solvent evaporation method has been used, but as the microparticles prepared by the solvent evaporation method have a particle size of 20 to 200 μm and are prepared such that the average diameter of the particles is not uniform, the aggregation among particles easily occurs, and at the time of administration as an injection, it is difficult to use microparticles as an injection dosage form as microparticles having a size sufficient for a foreign body sensation and pain to be increased are included.

In addition, the non-uniform average particle diameter may mean that the duration of drug release cannot be adjusted as desired.

That is, when an injection including microparticles having various particle sizes is administered to subcutaneous fat and muscle tissue, microparticles having small particle sizes are degraded in a short time, so that all of the drug included in the particles will be released into the body, and microparticles having a large particle size will release the drug for a longer time.

This may mean that it is actually impossible to control the drug release duration of a sustained release dosage form.

The microparticles prepared by the solvent evaporation method cannot precisely control the size of the microparticles due to the preparation method, and accordingly, there occurs a problem in that it is difficult to control a drug release duration that is suitable enough to actually treat a patient.

Preferably, the microparticles of the present invention are prepared by the preparation method described below, and in this case, a microchannel is used. The width length (w) and height length (d) of a microchannel cross section under Condition 1 to control the particle size need to be adjusted within a range of a ratio of average diameter to a predetermined length of microparticles to be prepared.

More specifically, the width (w) of the channel cross section needs to be set within a ratio range of 0.7 to 1.3 for an average diameter (d') of the microparticles, and the width of the channel cross section needs to be set within 70 to 130 μm in order to prepare microparticles having an average diameter (d') of 100 μm.

Further, the height (d) of the channel cross section needs to be set within a ratio range of 0.7 to 1.3 for an average diameter (d') of the microparticles, and the height of the channel cross section needs to be set within 70 to 130 μm in order to prepare microparticles having an average diameter (d') of 100 μm.

In order to prepare the microparticles of the present invention, a liquid mixture needs to be infused into the microchannel, and in this case, as the width (w) and height (d) of the microchannel cross section are adjusted as described above, microparticles having a desired size may be prepared.

The microparticles may maintain the effect of preventing or treating a cognitive impairment-related disease by sustainably releasing donepezil for 1 month.

The biodegradable polymer is selected from the group consisting of polylactic acid, polylactide, poly(lactic-co-glycolic acid), poly(lactide-co-glycolide)(PLGA), polyphosphazene, polyiminocarbonate, polyphosphoester, polyanhydride, polyorthoester, polycaprolactone, polyhydroxyvalerate, polyhydroxybutyrate, polyamino acid, and a combination thereof, and is not limited to the example.

More specifically, the preparing of the microparticles may include: 1) preparing a first mixture by dissolving a biodegradable polymer and donepezil in an organic solvent; 2) preparing a second mixture by dissolving a surfactant in water; 3) infusing the first mixture in Step 1) into a microchannel in a straight-line direction and allowing the first mixture to flow; 4) preparing microparticles in which donepezil is uniformly distributed in spherical biodegradable polymer particles by infusing the second mixture in Step 2) into a microchannel formed on both side surfaces or one side surface thereof and allowing the second mixture to flow such that the first mixture in Step 3) can form an intersection point with a microchannel flowing in a straight-line direction, and intersecting a flow of the first mixture in a straight-line direction with a flow of the second mixture; 5) collecting the microparticles produced at the intersection point in Step 4); 6) evaporating and removing an organic solvent present in the microparticles by stirring the microparticles collected in Step 5); and 7) washing the microparticles in Step 6) and drying the microparticles.

More specifically, in this case, when the first mixture is infused into a microchannel in a straight-line direction, the first mixture is infused under a certain pressure condition and allowed to flow at a certain flow rate, and in this case, the pressure condition is 600 to 1,000 mbar, preferably 800 mbar, but is not limited to the example. Further, when the second mixture is infused into a microchannel on both side surfaces or one surface, the second mixture is infused under a certain pressure condition and allowed to flow at a certain flow rate, and in this case, the pressure condition is 1,200 to 1,600 mbar, preferably 1,400 mbar, but is not limited to the example.

That is, in order to allow the second mixture forming an intersection point with the flow of the first mixture to flow at a faster flow rate than the first mixture to be infused into the microchannel in a straight-line direction, the second mixture is allowed to flow under a higher pressure condition.

As described above, the second mixture having a relatively faster flow rate compresses the first mixture at a point where the flow of the first mixture and the flow of the second mixture meet each other by varying the flow rates of the first mixture and the second mixture and making the flow rate of the second mixture faster than the flow rate of the first mixture, and in this case, due to repulsive force between the first mixture and the second mixture, the biodegradable polymer and donepezil in the first mixture form spherical microparticles, and more specifically, microparticles in which donepezil is uniformly distributed in the spherical biodegradable polymer are formed.

Thereafter, the collecting of the microparticles prevents aggregation of initially produced microparticles by collecting the microparticles in a bath including the second mixture.

The collecting of the microparticles uses the second mixture, that is, a mixed solution of a surfactant and water, and is used to prevent aggregation of collected microparticles by preparing the second mixture, and then infusing a portion of the second mixture into a microchannel, and transferring the other portion to a bath which collects the microparticles.

After the collecting of the microparticles, as a step of stirring microparticles collected in the bath, an organic solvent present on the surfaces of the microparticles is evaporated and removed by stirring the microparticles at a predetermined stirring rate under a predetermined temperature condition. In this case, the stirring step proceeds under the stirring condition in an order of firstly stirring the microparticles at a rate of 300 to 500 rpm at 15 to 20° C. for 0.5 to 2 hours; secondly stirring the microparticles at a rate of 500 to 800 rpm at 30 to 50° C. for 2 to 4 hours after the first stirring; and thirdly stirring the microparticles at a rate of 500 to 800 rpm at −1 to 2° C. for 0.5 to 1.5 hours after the second stirring. The stirring rate is 500 to 800 rpm, preferably 700 rpm, but is not limited to the example. The evaporation speed of the organic solvent present on the surface of the microparticles may be adjusted as the stirring process is performed by varying the stirring rate and temperature conditions for stirring the microparticles. That is, by evaporating the organic solvent present on the surface of the microparticle through the stirring process, the harmful solvent may be removed, and the microparticle having smooth surfaces may be prepared.

The temperature at which the first mixture and the second mixture flow in the microchannel is also 15 to 20° C., preferably 17° C. That is, after the mixtures flow in the microchannel and form an intersection point to produce microparticles, the temperature is constantly maintained at a low temperature of 15 to 20° C. until the collected microparticles are firstly stirred. Only when the low temperature is maintained during the process of preparing microparticles, it is possible to prepare and maintain spherical particles. That is, when the temperature is not under the low temperature condition, there occurs a problem in that it is difficult to prepare particles having a predetermined spherical shape.

Finally, as a step of washing the microparticles and drying the microparticles, the microparticles from which the organic solvent on the surfaces is completely removed by stirring are washed several times with purified water which is sterilized and filtered to remove the surfactant remaining in the microparticles, and are later lyophilized.

The microparticles may be prepared by infusing the mixture into the microchannel formed on a wafer and allowing the mixture to flow.

More specifically, aluminum is deposited onto a silicon wafer by using an e-beam evaporator, and a photoresist is patterned on aluminum by using a photolithography technique. Thereafter, the wafer is aluminum-etched by using a photoresist as a mask, silicon is etched by deep ion reactive etching (DRIE) by using aluminum as a mask after removing the photoresist, and glass is anodically bonded onto the wafer and hermetically sealed after removing aluminum, thereby manufacturing the aforementioned microchannel.

The organic solvent of the present invention is an organic solvent which is immiscible with water, is one or more selected from the group consisting of, for example, chloroform, chloroethane, dichloroethane, trichloroethane, and a mixture thereof, and is preferably dichloromethane, but the organic solvent is not limited to the example, and the organic solvent can dissolve a biodegradable polymer, and any organic solvent can be used as long as the organic solvent can be easily selected by a person with ordinary skill in the art without being limited to the aforementioned example.

The surfactant of the present invention can be used without limitation as long as the surfactant can help the biodegradable polymer solution form a stable emulsion. Specifically, the surfactant is one or more selected from the group consisting of a non-ionic surfactant, an anionic surfactant, a cationic surfactant, and a mixture thereof, and more specifically, the surfactant is one or more selected from the group consisting of methyl cellulose, polyvinylpyrrolidone, lecithin, gelatin, polyvinyl alcohol, polyoxyethylene sorbitan fatty acid esters, polyoxyethylene castor oil derivatives, sodium lauryl sulfate, sodium stearate, esters, amines, linear diamines, fatty amines, and a mixture thereof, and is preferably polyvinyl alcohol, but the surfactant is not limited to the example.

Advantageous Effects

The present invention is a pharmaceutical composition for preventing or treating a cognitive impairment-related disease, including donepezil or a method for preparing the same, and to eliminate the inconvenience of having to take a composition daily, a single injection can maintain the effect of preventing or treating a cognitive impairment-related disease for a month.

Further, as the present invention is prepared by maintaining the average diameters of the particles at a predetermined micrometer size, a foreign body sensation and pain during administration into a patient as an injection is reduced, thereby enabling administration as an injection to be facilitated.

BEST MODE

Figure 1:
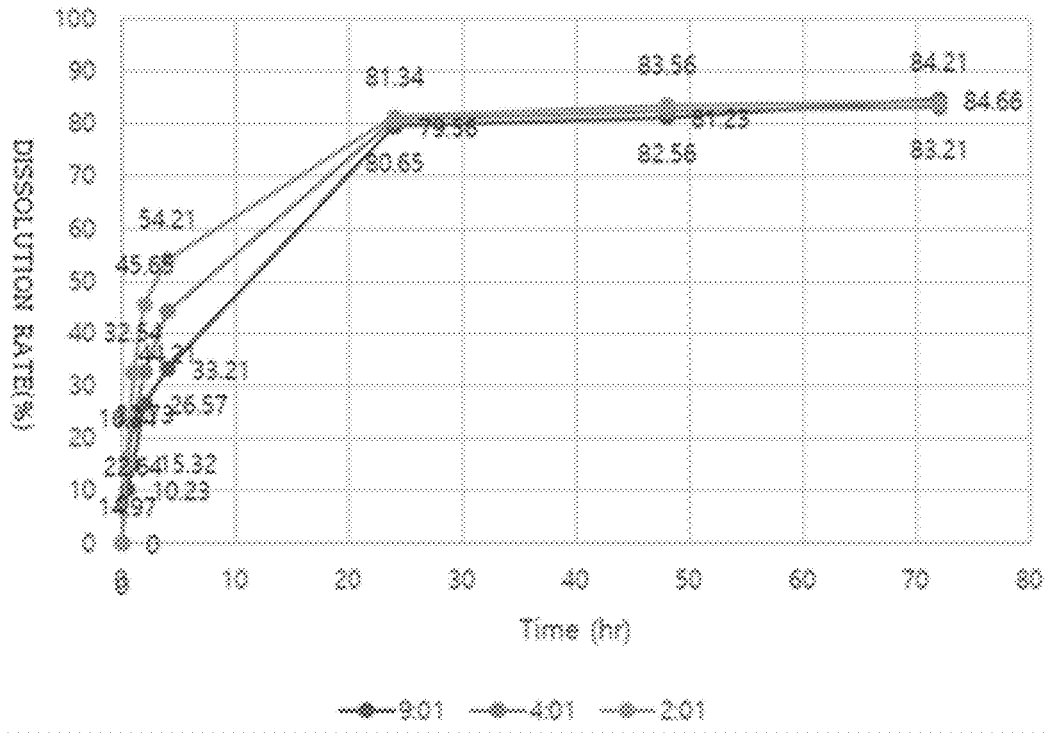
FIG. 1 is an experimental result for the amount of drug dissolved of the microparticles according to an exemplary embodiment of the present invention over time.

Hereinafter, the Examples of the present invention will be described in detail such that a person skilled in the art to which the present invention pertains can easily carry out the present invention. However, the present invention can be implemented in various different forms, and is not limited to the Examples described herein.

EXAMPLE 1

A first mixture was prepared by dissolving poly(lactide-co-glycolide)(PLGA) and a donepezil base in dichloromethane. In this case, the weight ratio of the poly(lactide-co-glycolide) and the donepezil base in the first mixture is 2:1.

As the poly(lactide-co-glycolide)(PLGA 7502), a biodegradable polymer in which a molar ratio of lactide and glycolide was 75/25 was used.

A second mixture including polyvinyl alcohol in an amount of 0.25 wt % was prepared by mixing a surfactant polyvinyl alcohol with water.

The first mixture and the second mixture were infused into a microchannel formed on a silicon wafer and allowed to flow. In this case, in order to allow the first mixture and the second mixture to flow at a certain flow rate, the first mixture and the second mixture were allowed to flow under a pressure condition of 800 mbar and under a pressure condition of 1,400 mbar, respectively. The temperature condition was maintained at 17° C.

Microparticles produced at an intersection point where the flow of the first mixture and the flow of the second mixture meet each other were collected in a bath comprising the second mixture. The microparticles collected in the bath were firstly stirred at a rate of 400 rpm at 17° C. for 1 hour, the temperature was increased to 40° C. and the microparticles were secondly stirred at a rate of 600 rpm for 3 hours, and then the temperature was decreased to 0° C. and the microparticles were thirdly stirred at a rate of 600 rpm for 1 hour.

The microparticles completely stirred were washed several times with purified water which was sterilized and filtered, and were lyophilized, thereby preparing microparticles.

EXAMPLE 2

Microparticles were prepared in the same manner as in Example 1, except that the poly(lactide-co-glycolide) and the donepezil base were included at a weight ratio of 4:1.

EXAMPLE 3

Microparticles were prepared in the same manner as in Example 1, except that poly(lactide-co-glycolide) and donepezil base were included at a weight ratio of 9:1.

EXAMPLE 4

Microparticles were prepared in the same manner as in Example 1, except that the poly(lactide-co-glycolide) and the donepezil base were included at a weight ratio of 1:1.

EXAMPLE 5

The poly(lactide-co-glycolide)(PLGA 5002) was prepared in the same manner as in Example 1, except that a biodegradable polymer in which the molar ratio of lactide and glycolide was 50/50 was used.

EXAMPLE 6

Microparticles were prepared in the same manner as in Example 1, except that the temperature condition during the stirring was set at 17° C. during the first stirring, 25° C. during the second stirring, and 40° C. during the third stirring.

EXAMPLE 7

Microparticles were prepared in the same manner as in Example 1, except that as the temperature condition during the stirring, an additional stirring process was performed at a rate of 600 rpm and 25° C. for 1 hour between the first stirring and the second stirring.

Experimental Example 1. Evaluation of Amount of Donepezil Dissolved over the Passage of Time 1. Release experiment according to contents of biodegradable polymer and drug (In-vitro)

About 100 mg of the microparticles in Examples 1 to 4 were put into a glass test container having a volume of 120 mL, and the container was filled with 100 mL of a release test solution. A drug release experiment was performed by putting the test container into a water bath at 45° C. and reciprocating the test container at an amplitude of 4 cm and a shaking frequency of 120 times/min as an experimental condition for acceleration of drug release. At the time of collecting the sample, the mixture was mixed by shaking the bottle well, and 1 mL of the sample was taken. After the sample was centrifuged at 13,000 rpm for 3 minutes, the supernatant was taken and analyzed with high performance liquid chromatography.

The drug release experimental results are shown in the following Table 1 and FIG. 1.

TABLE 1

|  | 0 (h) | 0.5 (h) | 1 (h) | 2 (h) | 4 (h) | 24 (h) | 48 (h) | 72 (h) |
|---|---|---|---|---|---|---|---|---|
| Example 3 | 0 | 10.23 | 15.32 | 26.57 | 33.21 | 79.56 | 81.23 | 84.66 |
| Example 2 | 0 | 14.97 | 22.64 | 32.73 | 44.21 | 80.65 | 82.56 | 83.21 |
| Example 1 | 0 | 16.34 | 32.54 | 45.65 | 54.21 | 81.34 | 83.56 | 84.21 |
| Example 4 |  |  |  | X |  |  |  |  |

(Unit dissolution rate %)

In the case of Example 4, it was confirmed that the biodegradable polymer and the drug were mixed at a ratio of 1:1 and that the microparticles themselves could not be prepared by the preparation method of the present invention. Thus, it was impossible to evaluate the dissolution rate over time.

In the case of Examples 2 and 3, the amount of drug initially released is so small that there was a problem in that as donepezil was released in vivo, the medicinal effect did not appear.

In the case of Example 1, an effective release amount could be exhibited even at the initial stage, and the degree to which the drug was released could be confirmed even after 72 hours elapsed, so that it could be confirmed that there was an effect for a long period of time.

2. Release experiment according to type of biodegradable polymer (In-vitro)

About 100 mg of the microparticles in Examples 1 to 5 were put into a glass test container having a volume of 120 mL, and the container was filled with 100 mL of a release test solution. A drug release experiment was performed by putting the test container into a water bath at 45° C. and reciprocating the test container at an amplitude of 4 cm and a shaking frequency of 120 times/min as an experimental condition for acceleration of drug release. At the time of collecting the sample, the mixture was mixed by shaking the bottle well, and 1 mL of the sample was taken. After the sample was centrifuged at 13,000 rpm for 3 minutes, the supernatant was taken and analyzed with high performance liquid chromatography.

Figure 2:
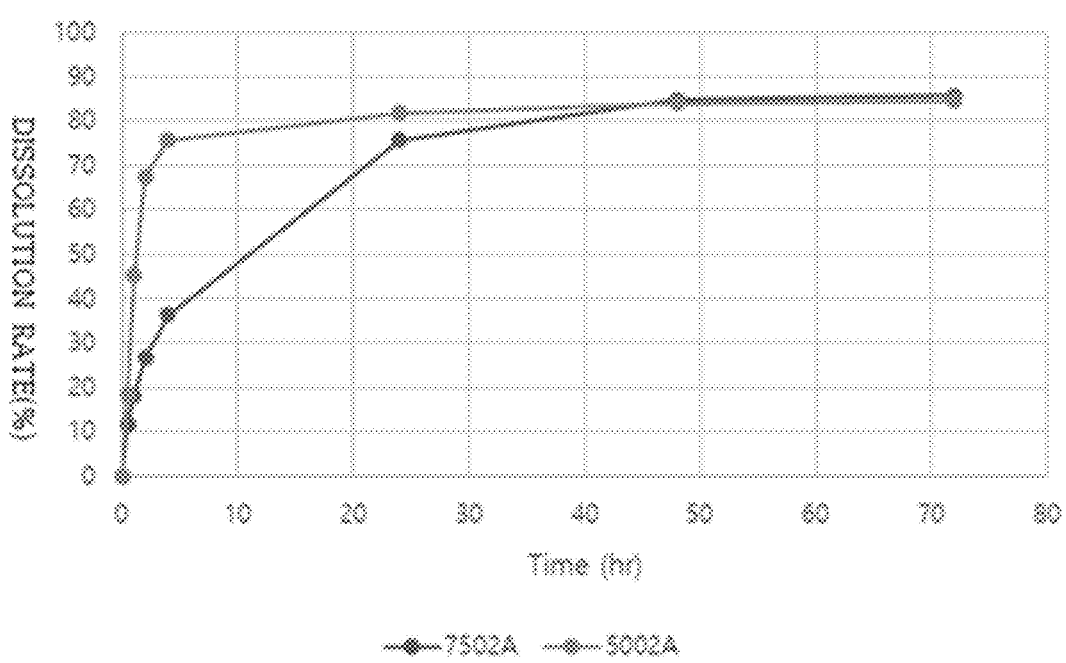
FIG. 2 is an experimental result for the amount of drug dissolved of the microparticles according to an exemplary embodiment of the present invention over time.

The drug release experimental results are as shown in the following Table 2 and FIG. 2.

TABLE 2

|  | 0 (h) | 0.5 (h) | 1 (h) | 2 (h) | 4 (h) | 24 (h) | 48 (h) | 72 (h) |
| --- | --- | --- | --- | --- | --- | --- | --- | --- |
| Example 1 | 0 | 11.73 | 18.18 | 26.57 | 36.33 | 75.69 | 84.74 | 85.64 |
| Example 5 | 0 | 18.23 | 45.32 | 67.54 | 75.62 | 81.78 | 83.97 | 84.56 |

(Unit dissolution rate %)

According to the experimental results, it could be confirmed that the degree to which the drug was released varied depending on the type of polymer. In the case of Example 5, the initial release amount was large, but after 24 hours, the degree to which the drug was released was so low that it could be said that Example 5 could not be used as a long-lasting dosage form.

In contrast, Example 1 could be used as a longer-lasting dosage form.

Experimental Example 2. Change in Properties of Microparticles

In order to confirm the change in properties of microparticles according to the stirring condition, SEM photographs of the microparticles prepared in the same manner as in Examples 1, 6, and 7 were confirmed.

Figure 3:
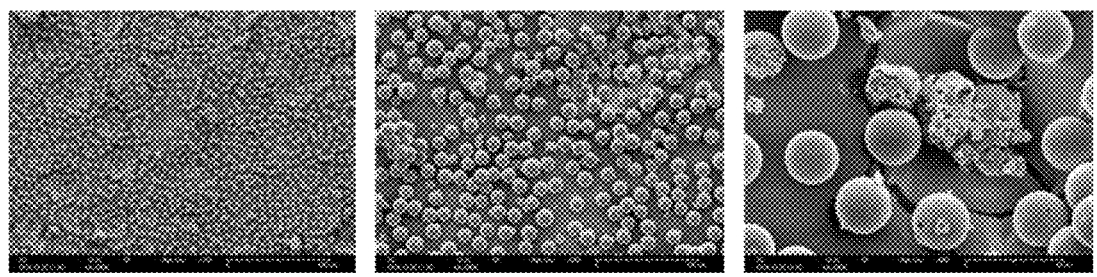
FIG. 3 is an SEM photograph of particles according to an exemplary embodiment of the present invention under each stirring condition.
Figure 4:
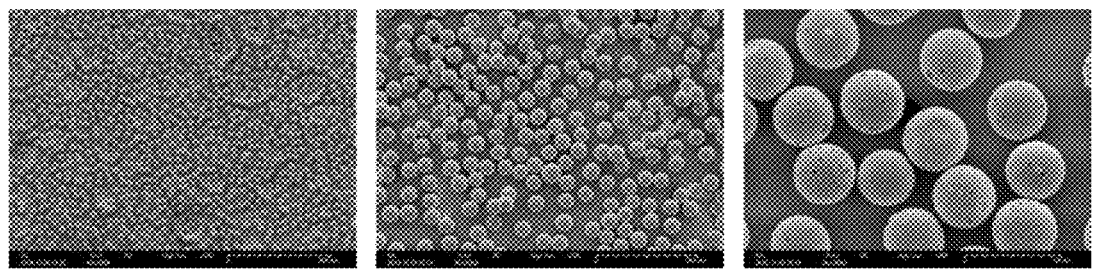
FIG. 4 is an SEM photograph of particles according to an exemplary embodiment of the present invention under each stirring condition.
Figure 5:
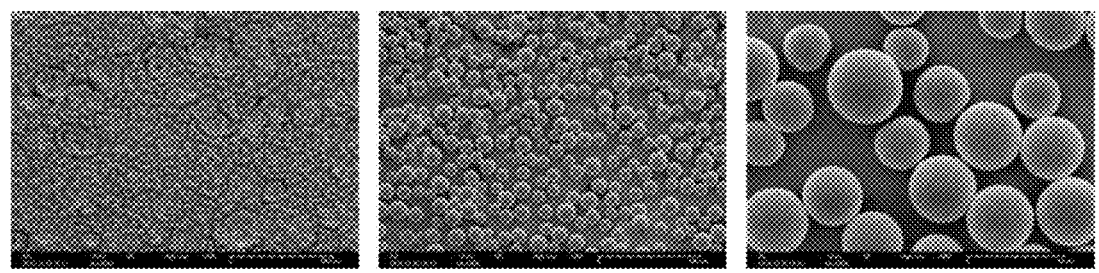
FIG. 5 is an SEM photograph of particles according to an exemplary embodiment of the present invention under each stirring condition.

The experimental results are illustrated in FIGS. 3 to 5.

FIG. 3 is the case where stirring was performed under the conditions of Example 6, and when stirring was not performed under 0° C. conditions as in Example 6, it was confirmed that the aggregation among particles occurred. Further, FIG. 4 is the case where stirring was performed under the conditions of Example 7, and when the stirring time was increased as in Example 7, it was confirmed that pores occurred on the surface of the particles, and thus there was a problem in that the surface was not uniformly formed.

In contrast, in the case of Example 1, as in FIG. 5, not only microparticles having a uniform particle diameter were prepared, but also the microparticles in which the surface was uniformly formed and the aggregation among particles did not occur could be prepared.

Experimental Example 3. Comparison Result of Blood Concentrations

The blood concentration of donepezil was measured over the passage of time by preparing the microparticles prepared in Example 1 as a long-lasting type injection dosage form, administering the dosage form to a beagle dog, collecting a blood sample. For comparison, blood concentrations were measured after a donepezil oral preparation was administered.

Figure 6:
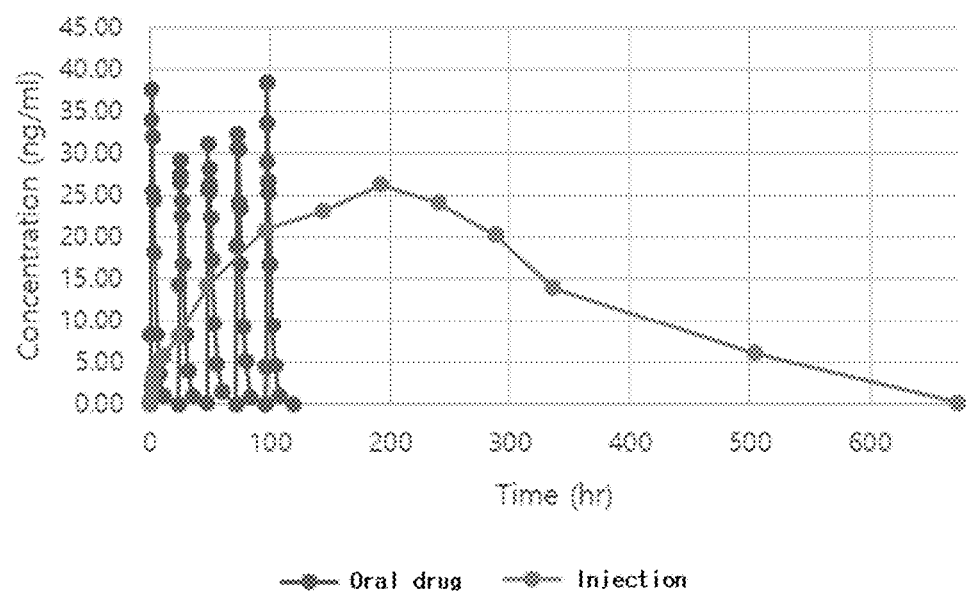
FIG. 6 is a comparison result of blood concentrations of microparticles according to an exemplary embodiment of the present invention when administered as an injection and orally administered.

The experimental results are illustrated in FIG. 6.

When donepezil was orally administered to a beagle dog, it was confirmed that the half-life is very short due to the effects of renal excretion and in vivo metabolic enzyme, and thus the blood concentration duration is very short for about one day, and thus, it was confirmed that even during the repeated administration, the drug lasting effect did not occur, but in the case of Example 1, it was confirmed that a single injection showed a constant blood concentration for a long period of time.

Although the preferred Examples of the present invention have been described in detail hereinabove, the right scope of the present invention is not limited thereto, and it should be understood that many variations and modifications of those skilled in the art using the basic concept of the present invention, which is defined in the following claims, will also fall within the right scope of the present invention.

The invention claimed is:

1. A method for preparing a pharmaceutical composition for treating a cognitive impairment-related disease, the method comprising:
   1) preparing a first mixture by dissolving a biodegradable polymer and donepezil in an organic solvent;
   2) preparing a second mixture by dissolving a surfactant in water;
   3) infusing the first mixture into a first microchannel in a straight-line direction and allowing the first mixture to flow;
   4) infusing the second mixture into a second microchannel formed on both side surfaces or one side surface and allowing the second mixture to flow so as to form an intersection point with the first microchannel, and intersecting a flow of the first mixture with a flow of the second mixture to form microparticles at the intersection point;
   5) collecting the microparticles produced at the intersection point;
   6) removing an organic solvent present on the surface of the microparticles by stirring the collected microparticles; and
   7) washing and drying the stirred microparticles, wherein in Step 6), the stirring the collected microparticles comprises a first stirring, a second stirring, and a third stirring, wherein the first stirring is performed at a rate of 300 to 500 rpm at 15 to 20° C. for 0.5 to 2 hours, the second stirring is performed at a rate of 500 to 800 rpm at 30 to 50° C. for 2 to 4 hours after the first stirring, the third stirring is performed at a rate of 500 to 800 rpm at −1 to 2° C. for 0.5 to 1.5 hours after the second stirring.

2. The method of claim 1, wherein the donepezil is comprised in a form of donepezil or a pharmaceutically acceptable salt thereof.

3. The method of claim 1, wherein the microparticles have an average diameter of 30 to 70 μm.

4. The method of claim 1, wherein the microparticles maintain the effect of preventing or treating a cognitive impairment-related disease by sustainably releasing donepezil for 1 month.

5. The method of claim 1, wherein the biodegradable polymer is selected from the group consisting of polylactic acid, polylactide, poly(lactic-co-glycolic acid), poly(lactide-co-glycolide)(PLGA), polyphosphazene, polyiminocarbonate, polyphosphoester, polyanhydride, polyorthoester, polycaprolactone, polyhydroxyvalerate, polyhydroxybutyrate, polyamino acid, and a combination thereof.

6. The method of claim 1, wherein
   a width (w) of a cross section of each of the first microchannel and the second microchannel is within a ratio range of 0.7 to 1.3 for an average diameter (d') of the microparticles.

7. The method of claim 1, wherein
a height (d) of a cross section of each of the first microchannel and the second microchannel is within a ratio range of 0.7 to 1.3 for an average diameter (d') of the microparticles.

8. The method of claim 1, wherein the cognitive impairment-related disease is dementia, Alzheimer's disease, amnesia, or Parkinson's disease.

* * * * *